US009246105B2

(12) United States Patent
Sun

(10) Patent No.: US 9,246,105 B2
(45) Date of Patent: Jan. 26, 2016

(54) FLUORINATED AROMATIC MATERIALS AND THEIR USE IN OPTOELECTRONICS

(71) Applicant: The University of South Dakota, Vermillion, SD (US)

(72) Inventor: Haoran Sun, Vermillion, SD (US)

(73) Assignee: The University of South Dakota, Vermillion, SD (US)

( * ) Notice: Subject to any disclaimer, the term of this patent is extended or adjusted under 35 U.S.C. 154(b) by 0 days.

(21) Appl. No.: 14/675,133

(22) Filed: Mar. 31, 2015

(65) Prior Publication Data
US 2015/0207078 A1  Jul. 23, 2015

Related U.S. Application Data

(62) Division of application No. 13/391,375, filed as application No. PCT/US2010/046207 on Aug. 20, 2010, now Pat. No. 9,024,094.

(60) Provisional application No. 61/235,970, filed on Aug. 21, 2009.

(51) Int. Cl.
| | |
|---|---|
| H01L 51/00 | (2006.01) |
| C07C 17/32 | (2006.01) |
| C07C 25/22 | (2006.01) |
| C07D 471/04 | (2006.01) |
| C07C 17/20 | (2006.01) |
| C07C 22/08 | (2006.01) |
| C07C 41/22 | (2006.01) |
| C07C 43/12 | (2006.01) |
| C09B 1/10 | (2006.01) |
| C07D 517/00 | (2006.01) |
| H01L 51/05 | (2006.01) |
| H01L 51/42 | (2006.01) |
| H01L 51/50 | (2006.01) |

(52) U.S. Cl.
CPC .......... *H01L 51/0052* (2013.01); *C07C 17/202* (2013.01); *C07C 17/32* (2013.01); *C07C 22/08* (2013.01); *C07C 25/22* (2013.01); *C07C 41/22* (2013.01); *C07C 43/126* (2013.01); *C07D 471/04* (2013.01); *H01L 51/0072* (2013.01); *C07C 2103/24* (2013.01); *C07D 517/00* (2013.01); *C09B 1/10* (2013.01); *H01L 51/0558* (2013.01); *H01L 51/42* (2013.01); *H01L 51/5012* (2013.01)

(58) Field of Classification Search
None
See application file for complete search history.

(56) References Cited

U.S. PATENT DOCUMENTS

| 5,580,488 A | 12/1996 | Nakamura et al. |
| 6,048,827 A | 4/2000 | Fukuchi |

FOREIGN PATENT DOCUMENTS

| EP | 1737027 A1 | 12/2006 |
| JP | 05170689 A1 | 9/1993 |
| WO | 2004035551 A2 | 4/2004 |

OTHER PUBLICATIONS

International Search Report and Written Opinion issued in PCT/US2010/046207, dated Nov. 26, 2010, 22 pgs.
Betzemeier, B. et al., A Selenium Catalyzed Epoxidation in Perfluorinated Solvents with Hydrogen Peroxide, Synlett, 1999, pp. 489-491, 3 pgs.
Bingnan, Huang et al., A Facile Method for the Perfluoroalkylation of Pyridine and its Derivatives, Tetrahedron Letters, vol. 31, No. 19, 1990, pp. 2711-2712, 2 pgs.
Chen, G.J. et al. Perfluoroalkylations and Perfluorooxaalkylkations. Part 3. Chloro-substituted Diazines as Substrates in Copper-mediated Cross-coupling, Journal of Fluorine Chemistry, vol. 73, No. 1, Jul. 1, 1995, pp. 113-119, 7 pgs.
Chen, G.J., Polyfluoralkylation of Bromoaromatic Compounds via Perfluoroalkylcopper Intermediates; Journal of Fluorine Chemistry, vol. 43, No. 2, May 1, 1989, pp. 207-228, 22 pgs.
Chen, Liang et al., Fluoroalkylation of Porphyrins: Generation of 2- and 20-Perfluoroalkyl-5, 10, 15-triarylporphyrin Radicals and their Intramolecular Cyclizations, Synlett, No. 6, 2005, 8 pgs.
Huang, X-T et al., Fluoroalkylation of Aromatic Compounds with Per (poly)fluoroalkyl Chlorides Initiated by Sodium Dithionite in DMSO, Journal of Fluorine Chemistry, 7 pgs.
Kiss, L.E. et al., An Improved Design of Fluorophilic Molecules: Prediction of the 1n P fluorous Partition Coefficient, Fluorophilicity, using 3D QSAR Descriptors and Neural Networks, Journal of Fluorine Chemistry, vol. 108, 2001, pp. 95-109, 15 pgs.
Li, Ling et al., Tuning the Electronic Structure of Conjugated Polymers with Fluoroalkyl Substitution: Alternating Alkyl/Perfluoroalkyl-Substituted Polythiophene, vol. 38, No. 2, Jan. 25, 2005, pp. 372-378, 7 pgs.
Umemoto, Teruo et al., Perfluoroalkylation of Aromatic Compounds with Rfl(Ph)OSO2CF3, Chemistry Letters, 1981, pp. 1663-1666, 4 pgs.
Uno, H. et al., A Novel Method for the Synthesis of 4-Isoquinolinois, Journal of Heterocyclic Chemistry, vol. 28, No. 2, Jan. 1, 1991, pp. 341-346, 6 pgs.
Vickic-Topic, D. et al., Photochemical Synthesis and NMR Analysis of Novel Regiospecifically Trifluoromethyl-Substituted Dibenzosemibullvalene, Journal of Fluorine Chemistry, vol. 74, No. 1, Sep. 1, 1995, pp. 159-164, 6 pgs.

*Primary Examiner* — James Rogers
(74) *Attorney, Agent, or Firm* — Faegre Baker Daniels LLP

(57) ABSTRACT

Fluorinated aromatic materials, their synthesis and their use in optoelectronics. In some cases, the fluorinated aromatic materials are perfluoroalkylated aromatic materials that may include perfluoropolyether substituents.

4 Claims, 3 Drawing Sheets

FLUORINATED AROMATIC MATERIALS AND THEIR USE IN OPTOELECTRONICS

CROSS-REFERENCE TO RELATED APPLICATION

This application is a divisional application of U.S. application Ser. No. 13/391,375, filed on May 2, 2012, which is a National Stage Entry of PCT/US2010/046207, filed on Aug. 20, 2010, which claims the benefit of provisional patent application Ser. No. 61/235,970, entitled "FLUORINATED AROMATIC MATERIALS AND THEIR USE IN OPTOELECTRONICS," filed on Aug. 21, 2009. The entire disclosures of which are hereby expressly incorporated by reference.

STATEMENT REGARDING FEDERALLY SPONSORED RESEARCH OR DEVELOPMENT

The United States government may have certain rights to this invention.

TECHNICAL FIELD

The disclosure pertains generally to fluorinated aromatic materials, their synthesis and their use in optoelectronics.

BACKGROUND

Fluorinated aromatics and related materials offer many advantages over non-fluorinated materials in a variety of different optoelectronic devices such as, but not limited to, organic light emitting diodes, organic field-effect transistors, organic solar cells, and dye-sensitized solar cells. These fluorinated materials have processing advantages and are thermally and photochemically stable. They have reduced flammability tolerance to extreme environmental conditions, including superhydrophobicity and oleophobicity. Fluorinated materials also have advantages in tuning the electronic and optical properties of these devices. For example, these materials can be used to produce oxygen stable n-type semiconductors that can be used in organic solar cells, dye-sensitized solar cells, polymer solar cells, organic light emitting diodes (OLEDs), organic thin-film field-effect transistors (OFETs).

SUMMARY

The invention is directed to fluorinated aromatic materials, their synthesis and their use in optoelectronics. In some embodiments, the fluorinated aromatic materials are perfluoroalkylated aromatic materials that may include perfluoropolyether substituents.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
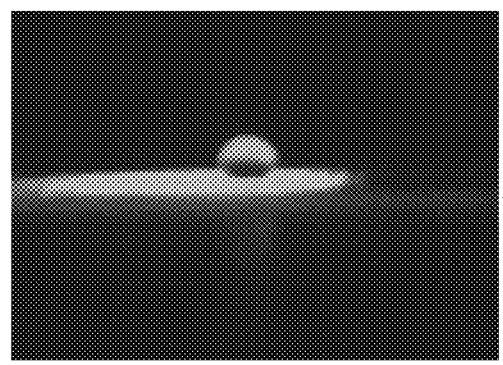
FIG. 1 is an electronic image illustrating hydrophobicity.
Figure 2:
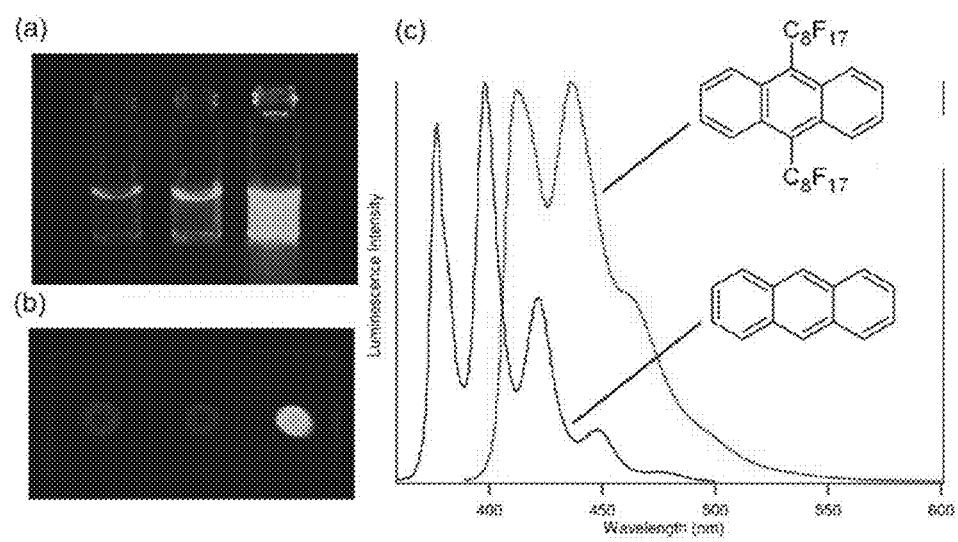
FIG. 2 is an electronic image illustrating luminescence.

Fluorinated materials such as fluorinated aromatic materials have strongly enhanced luminescence, higher chemical stability and higher photostability when compared to corresponding non-fluorinated aromatic materials. Fluorinated aromatic materials are also highly hydrophobic and oleophobic, which may be useful in limiting proton-related reduction of the aromatic. FIG. 1 illustrates the hydrophobic nature of fluorinated materials. In FIG. 1, a water drop is seen on a solid perfluoroalkylated dye covered glass slide. FIG. 2 illustrates the luminescence. In FIGS. 2A and 2B, the photoluminescence of, from left to right, anthracence, 9,10-dibromo anthracene and 9,10-bis(perfluorooctyl)anthracene is seen. FIG. 2C provides a graphical representation of luminescence intensity for anthracene and 9,10-bis(perfluorooctyl)anthracene.

Figure 3:
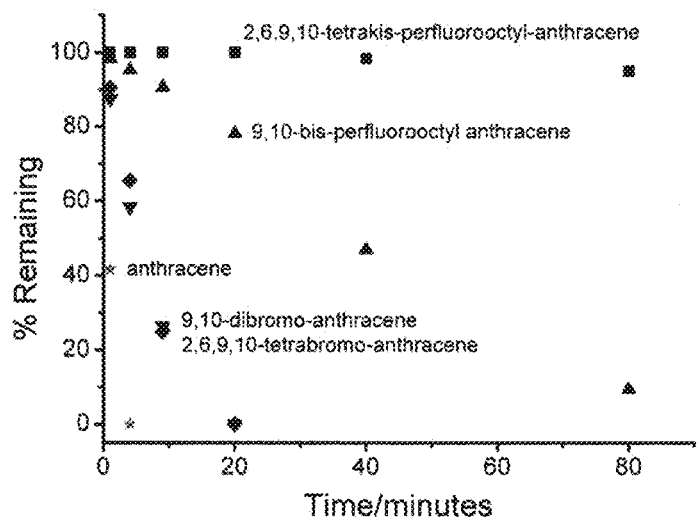
FIG. 3 is a graph illustrating the photostability of perfluoroalkylated anthracenes.
Figure 4:
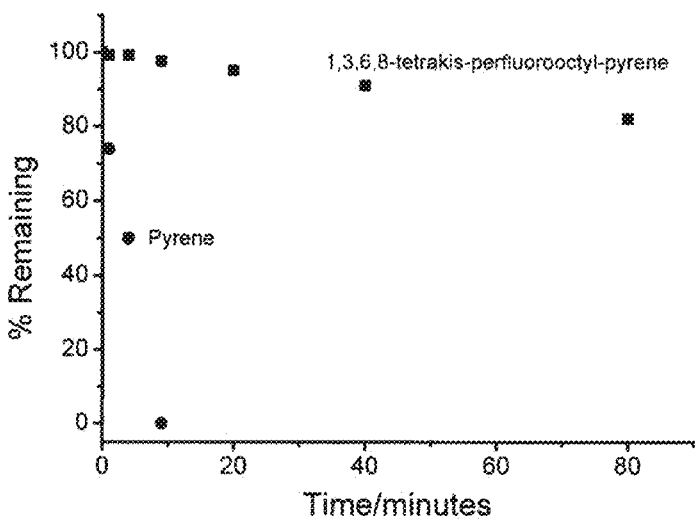
FIG. 4 is a graph illustrating the photostability of perfluoroalkylated pyrenes.

FIGS. 3 and 4 illustrate the photostability of the fluorinated aromatic materials described herein. In FIGS. 3 and 4, the materials were tested with a 300 W Xe light with a 1.5 AM filter. The Y axis shows the percentage of the tested compounds remaining after being exposed to light for a particular amount of time. FIG. 3 compares fluorinated and non-fluorinated anthracene derivatives while FIG. 4 compares fluorinated and non-fluorinated pyrene derivatives.

In some embodiments, the fluorinated aromatic materials have fluorinated side chains that include $sp^3$ hydridized carbon atoms. In some embodiments, $C_{sp3}$—F functional groups are much more chemically resistant than $C_{sp2}$—F functional groups, which in some cases are susceptible to nucleophilic aromatic substitution when strong nucleophiles are present. Although the $C_{sp2}$—F bond is stable against oxidation, it can undergo reductive defluorination, especially when reducing metals and reagents are present or under electrochemical reducing conditions.

In some embodiments, the fluorinated aromatic materials are perfluoroalkylated aromatic materials that may include perfluoropolyether substituents. These materials may include at least one perfluoroalkyl group or semi-perfluoroalkyl group on the aromatic core structure. Illustrative but non-limiting examples of aromatic core structures include pyrroles, thiophenes, benzenes, naphthalenes, anthracenes, acenaphthene, acenaphthylene, fluorene, phenalene, phenanthrene, benzo[a]anthracene, benzo[a]fluorine, benzo[c]phenanthrene, chrysene, fluoranthene, pyrenes, tetracenes, triphenylene, anthanthrene, benzopyrene, benzo[a]pyrene, benzo[e]pyrene, benzo[b]fluoranthene, benzo[j]fluoranthene, benzo[k]fluoranthene, benzo[ghi]perylene, corannulene, coronene, dicoronylene, diindenoperylene, helicene, heptacene, hexacene, kekulene, ovalene, pentacene, perylene, picene, tetraphenylenepentacenes, fullerenes, bi-pyridines, ter-pyridines, quinolines, phenanthrolines, porphyrins, benzoporphyrins, and phthalocyanines.

In some embodiments, fluorinated aromatic materials may be of the formula:

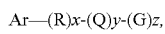

where Ar is an aromatic core including 3 to about 120 $sp^2$ hybridized carbon atoms or a total of 3 to about 120 $sp^2$ hybridized carbon atoms, nitrogen atoms, oxygen atoms and sulfur atoms; R is a perfluoroalkyl group of the formula $C_nF_{2n+1}$, n is an integer ranging from 1 to about 30; Q is a perfluoropolyether group of the formula $C_kF_{2k+1}O_h$, k is an integer ranging from 1 to about 1000, h is an integer less than or equal to k−1; G is an organic functional group selected from the group consisting of hydrogen, $C_{1-30}$ alkyl, $C_{3-30}$ aryl, halogen, nitro, cyano, ester, ether, hydroxyl, aryl group bearing substituents including one or more of carbon, fluorine, chlorine, bromine, nitro or methoxy, or an aryl group including a heteroatom such as N, O and S; x, y and z are integers such that x+y+z is less than or equal to the total number of $sp^2$ hybridized carbon atoms, nitrogen atoms, oxygen atoms and sulfur atoms within the aromatic core, and y and z may independently be zero.

In some embodiments, the aromatic core may be selected from the group consisting of benzene, naphthalene, anthracene, pyrene, coronene, phenanthroline, bi-pyridine and ter-pyridine. In some embodiments, R may be $C_8F_{17}$ and x is in the range of 2 to 6. In some embodiments, G may be hydrogen, $C_{1-30}$ alkyl, $C_{3-30}$ aryl, halogen, nitro, cyano, ester, ether or hydroxyl.

In some embodiments, the perfluoroalkylated heterocyclic aromatics may form metal complexes with metals such as Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Au, Hf, Ta, W, Re, Os, Ir, Pt, Au, Hg, and lanthanides with formal oxidation states from +1 to +6. In some embodiments, the heterocyclic aromatic cores may be selected from the group consisting of phenanthroline, bi-pyridine, ter-pyridine, and quinoline. In some embodiments, a metal complex may be one or more molecules selected from the group consisting of

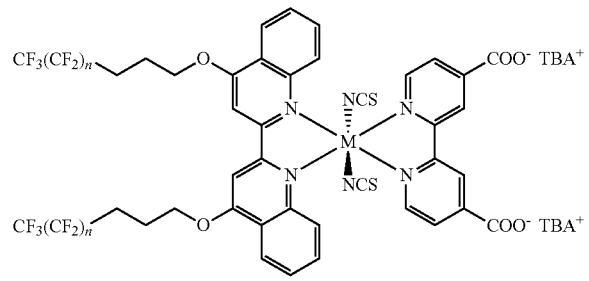

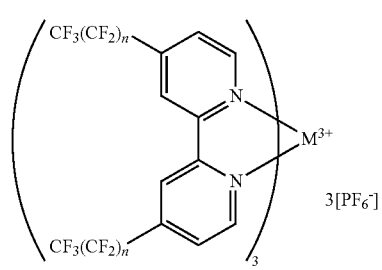

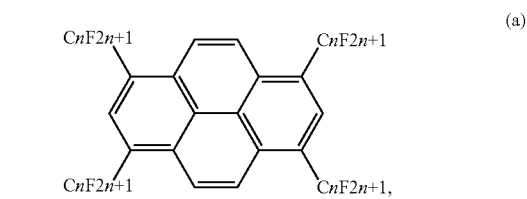

in which n may be between about 1 and about 30.

In some embodiments, a fluorinated aromatic material may be one or more molecules selected from the group consisting of:

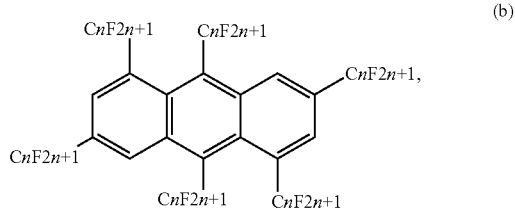

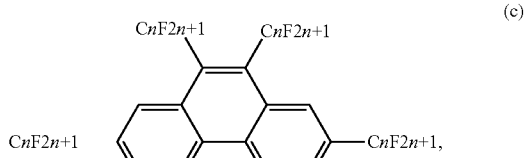

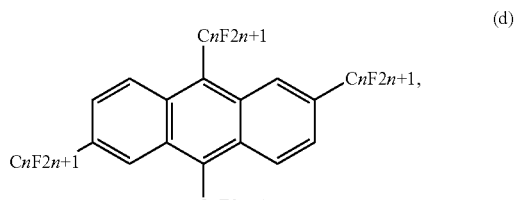

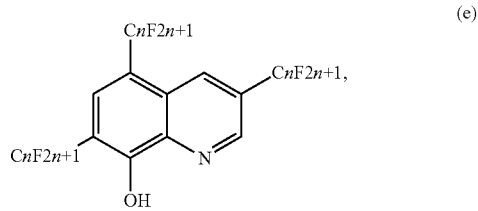

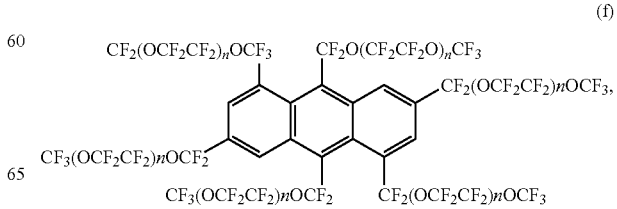

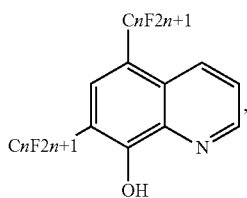
(g)

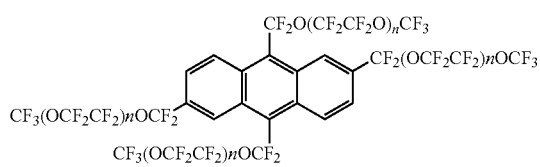
(h) and

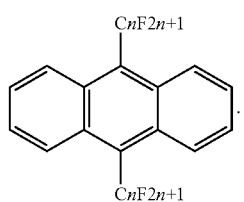
(j)

In some embodiments, n is between about 1 and about 30. In other embodiments, n is between about 2 and about 30.

In some embodiments, a fluorinated aromatic material may be 9,10-bis-perfluorooctyl anthracene, which has the structure:

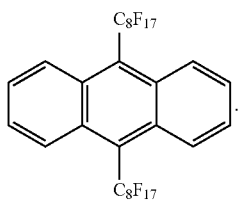
(a)

In some embodiments, a fluorinated aromatic material may be 1,3,6,8-tetrakis perfluorooctyl pyrene, which has the structure:

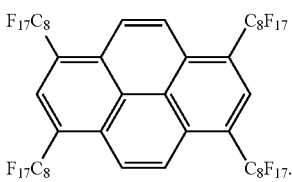
(c)

In some embodiments, a fluorinated aromatic material may be 2,6,9,10-tetrakis-heptadecafluorooctyl-anthracene, which has the structure:

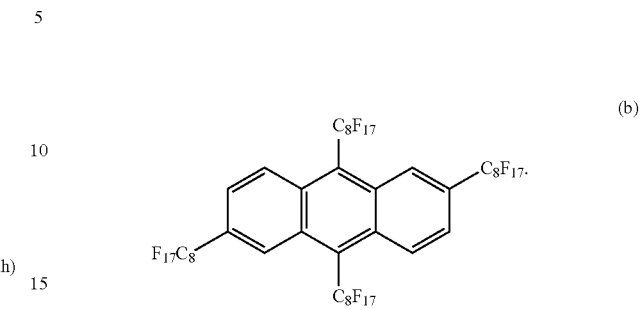
(b)

In some embodiments, a fluorinated aromatic compound may be 5,6-bisperfluorooctyl-1,10-phenanthroline, which has the structure:

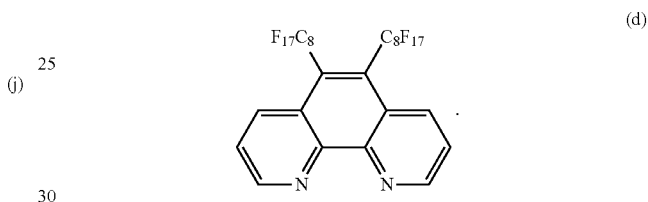
(d)

In some embodiments, perfluoroalkylated and semi-perfluoroalkylated aromatics and heterocyclic aromatics and related polymers may be synthesized via transition metal mediated/catalyzed cross-coupling reactions from corresponding halogenated aromatic precursors (Ar—X, where X is F, Cl, Br or I) and perfluoroalkyl halide (RfX, where X is Cl, Br or I). In some embodiments, the perfluoroalkylation reaction may be copper mediated and may be carried out under a nitrogen atmosphere. In some embodiments, the perfluoroalkyl group may be abbreviated as $C_nF_{2n+1}$ in which n is an integer between 1 and 18 and the semi-perfluoroalkyl group may be abbreviated as $C_mH_{2m}C_nF_{2+1}$ in which m is an integer between 1 and 3 and n is an integer between 1 and 17.

In some embodiments, polar aprotic solvents, such as DMSO or DMF, with cupper mediator, work well for many aromatic halides (bromide and iodide). However, since DMSO and DMF are fluorophobic instead of fluorophilic, the reaction intermediates of perfluoroalkylated compounds are almost insoluble in these fluorophobic solvents. The insolubility of the reaction intermediates lead to an incomplete reaction and multiple side products, including isomers that are very difficult to separate.

In some embodiments, polar fluorophilic solvents (e.g. benzotrifluoride) may be used as co-solvents to dissolve the reaction intermediates. As a result, the perfluoroalkylation reaction goes to completion and gives almost exclusively the target product for most of the reactions under optimized conditions. Examples of suitable polar fluorophilic solvents include benzotrifluoride and the fluorinated ethers available commercially from 3M under the tradenames HFE-7100®, HFE-7200® and HFE-7500®.

In some embodiments, perfluoroalkylated aromatic materials may be made in accordance with the following reaction scheme:

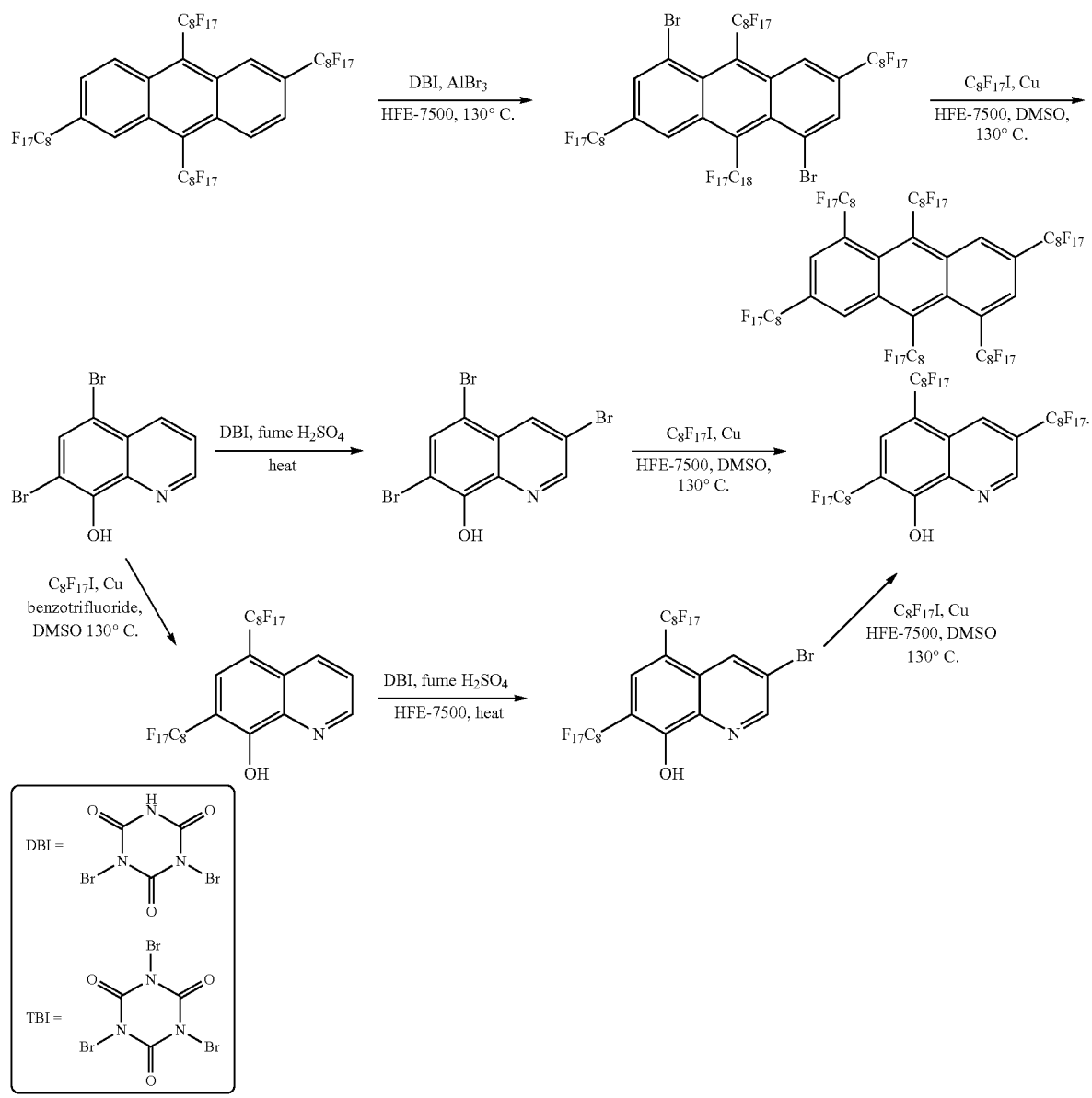

In some embodiments, perfluoroalkylated aromatic materials may be directly synthesized by perfluoroalkylating a brominated aromatic molecule. In some embodiments, perfluoroalkylated aromatic materials may be synthesized through a stepwise bromination, perfluoroalkylation, further bromination and so on.

The fluorinated aromatic materials described herein may be used in a variety of optoelectronic devices. Illustrative but non-limiting examples of suitable uses include organic solar cells, dye-sensitized solar cells, polymer solar cells, organic light emitting diodes (OLEDs), organic thin-film field-effect transistors (OFETs), laser diodes, two-photon absorption materials, multifunctional biomedical imaging reagents including reagents for MRI, ultrasounds, NIR fluorescence, photodynamic therapy and others. In some embodiments, these materials may be used to form air stable and moisture resistant n-type semiconductors.

Figure 5:
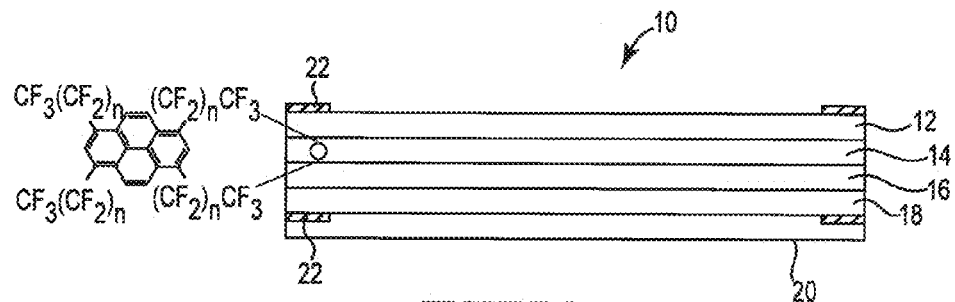
FIG. 5 is a schematic illustration of a heterojunction organic blue light emitting diode (OLED).

FIG. 5 is a schematic illustration of a heterojunction organic blue light emitting diode (OLED) 10 that utilizes both fluorinated and non-fluorinated materials. The OLED 10 may be constructed via chemical vapor deposition, physical vapor deposition and a thickness-controlled spin coating method in which the thickness of each element and layer is controlled. The OLED 10 includes a conducting carbon fiber cathode 12 and a fluorinated n-type semiconductor 14. Commercial carbon fiber may be used for the conducting carbon fiber cathode 12. The fluorinated n-type semiconductor 14 may be formed of a perfluoroalkylated pyrene of the structure shown, in which n may be an integer ranging from about 0 to about 17. The OLED 10 includes a p-type non-fluorinated semiconductor 16 that may, in some embodiments, be formed of the same material as the n-type semiconductor 14 but without the perfluoroalkyl substituent groups. The OLED 10 may include a perfluoroalkylated conducting polymer anode 16 and a conducting glass or polymer substrate 18. Printed silver wire is used as the electrical connectors 22. The perfluoroalkylated conducting polymer anode 16 may be formed of poly 3,4- perfluoroalkyl pyrroles and/or poly 3,4-perfluoroalkyl thiophenes having the following structures:

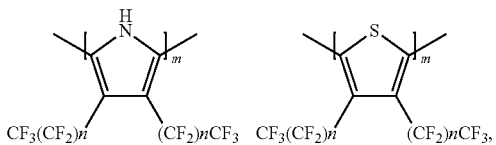

in which n is in the range of about 1 to about 30 and mi is in the range of about 1 to about 10,000.

Figure 6:
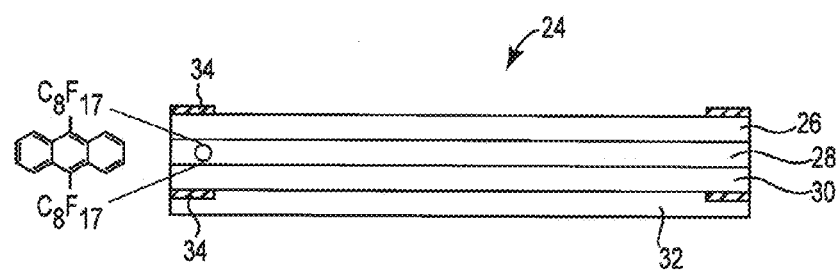
FIG. 6 is a schematic illustration of a homojunction organic blue light emitting diode (OLED).

FIG. 6 is a schematic illustration of a homojunction organic blue light emitting diode (OLED) 24 that includes fluorinated aromatic materials such as those discussed above. The OLED 24 may be constructed via chemical vapor deposition, physical vapor deposition and a thickness-controlled spin coating method in which the thickness of each element and layer is controlled. The OLED 24 includes a conducting carbon fiber cathode 26 formed of commercial conducting carbon fiber and a fluorinated n-type semiconductor 28. The fluorinated n-type semiconductor 28 may be formed of a perfluoroalkylated anthracene of the structure shown. The OLED 24 may include a perfluoroalkylated conducting polymer anode 30 and a conducting glass or polymer substrate 32. Printed silver wire is used as the electrical connectors 34. The perfluoroalkylated conducting polymer anode 30 may be formed of the poly 3,4-perfluoroalkyl pyrroles and poly 3,4-perfluoroalkyl thiophenes described above with respect to FIG. 5.

Figure 7:
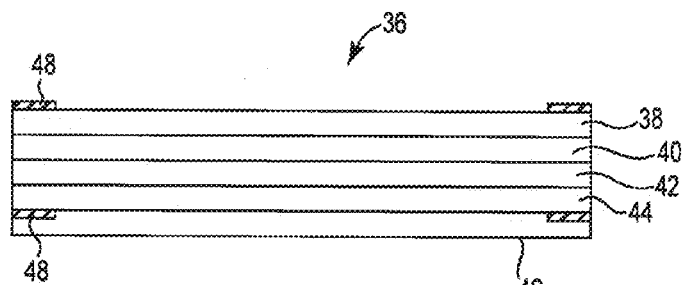
FIG. 7 is a schematic illustration of a heterojunction flexible organic solar cell (OSC).

FIG. 7 is a schematic illustration of a heterojunction flexible organic solar cell (OSC) 36 that is constructed using fluorinated aromatic materials (e.g. perfluoroalkylated porphyrins, perfluoroalkylated benzoporphyrins, and perfluoroalkylated phthalocyanines), fluorinated polymers, and non-fluorinated materials as p-type semiconductors (e.g. benzoporphyrins, phthalocyanines). The OSC 36 may be constructed via chemical vapor deposition, physical vapor deposition and a thickness-controlled spin coating method in which the thickness of each element and layer is controlled. The OSC 36 includes a perfluoroalkylated (e.g. poly 3,4-perfluoroalkyl thiophene) conducting polymer cathode 38 and a fluorinated n-type semiconductor 40 that may be formed of any of the fluorinated aromatic materials discussed herein. The OSC 36 includes a non-fluorinated p-type semiconductor 42 and a perfluoroalkylated conducting polymer anode 44. The OSC 36 includes a conducting substrate 46. Printed silver wire is used as the electrical connectors 48. The perfluoroalkylated conducting polymer anode 44 may be formed of the poly 3,4-perfluoroalkyl pyrroles and poly 3,4-perfluoroalkyl thiophenes described above with respect to FIG. 5.

EXAMPLES

Example 1

Synthesis of 1,3,6,8-Tetrakis-perfluorooctyl-pyrene

Perfluorooctyl iodide ($C_8F_{17}I$, 1.10 ml, 4.13 mmol) was added into a mixture of 1,3,6,8-Tetrabromopyrene (0.146 g, 0.25 mmol) and copper powder (0.525 g, 8.26 mmol) in α,α,α-trifluorotoluene and anhydrous DMSO under nitrogen protection at 130-135° C. 1,3,6,8-Tetrabromopyrene was prepared from pyrene through direct bromonation. The reaction was monitored by TLC and quenched after 5 hours with acidic ice water. The mixture was suction filtered and the precipitate was washed at least three times with hydrochloric acid and D.I. water, then the solid crude product (ash gray) was further extracted with HFE-7200® to yield white crystalline 1,3,6,8-tetrakis-perfluorooctyl-pyrene (0.363 g, 75%) with bright blue fluorescence. Characterization data: 1H-NMR: 8.65 ppm (1H) and 8.82 ppm (2H).

Example 2

Synthesis of 2,6,9,10-tetrakis-heptadecafluorooctyl-anthracene

Perfluorooctyl iodide ($C_8F_{17}I$, 3.28 ml, 12.4 mmol) was added into a mixture of 2,6,9,10-tetrabromoanthracene (0.494 g, 1 mmol) and copper powder (1.576 g, 24.8 mmol) in α,α,α-trifluorotoluene and anhydrous DMSO under nitrogen protection at 130-135° C. 2,6,9,10-tetrabromoanthracene was prepared from anthracene through direct bromonation. The reaction was monitored by TLC and quenched after 4 hours with ice water. The mixture was worked up with standard extraction methylene chloride and toluene and filtration to give 2,6,9,10-tetrakis-heptadecafluorooctyl-anthracene in good yield. mp 94-96° C.

Characterization data: 1H NMR ($CDCl_3$): δ 9.00 ppm (s, 2H), 8.75 ppm (d, 2H), 7.85 ppm (d, 2H); 19F NMR ($CDCl_3$); δ −80.57 ppm (t, 23.34 Hz, 12F), −90.91 ppm (m, 8F), −111.62 ppm (m, 8F), −116.81 ppm (m, 8F), −121.46 ppm (m, 8F), −121.84 ppm (m, 8F), −122.86 ppm (m, 8F), −126.08 ppm (m, 8F); MS (LRFAB pos ion); m/z (m+) 1850.0 (calcd for $C_{46}H_6F_{68}$: 1850.4): C, H analysis; Calcd (%) for $C_{46}H_6F_{68}$ is C, 29.85; H, 0.32. found C, 29.67; H, 0.19.

Example 3

Synthesis of 9,10-bis-perfluorooctyl-anthracene

Perfluorooctyl iodide ($C_8F_{17}I$, 2.36 ml, 8.93 mmol) was added into a mixture of 9,10-dibromoanthracene (0.6 g, 1.78 mmol) and copper powder (1.14 g, 17.8 mmol) in trifluorotoluene and anhydrous DMSO under nitrogen protection at 130° C. 9.10-dibromoanthrocene is commercially available. The reaction was monitored by TLC and quenched after 4 hours with ice water. The mixture was worked up with standard extraction with methylene chloride to give 9,10-bis-perfluorooctyl-anthracene in good yield.

Characterization data: mp 128-132° C.; 1H NMR ($CDCl_3$): δ 8.42 ppm (d, 4H), 7.61 ppm (d, 4H); 19F NMR ($CDCl_3$); δ −80.56 ppm (t, 21.36 Hz, 6F), −90.86 ppm (m, 4F), −116.68 ppm (m, 4F), −121.21 ppm (m, 4F), −121.57 ppm (m, 4F), −122.88 ppm (m, 4F), −125.88 ppm (m, 4F), −125.91 ppm (m, 8F); MS (LRFAB pos ion); m/z (m+) 1014.0 (calcd for $C_{30}H_8F_{34}$: 1014.3): C, H analysis; Calcd (%) for $C_{30}H_8F_{34}$ is C, 35.52; H, 0.78. found C, 35.17; H, 0.74.

Example 4

Synthesis of 5,6-bisperfluorooctyl-1,10-phenanthroline 0.5 g (1.47 mmol) of 5,6-dibromo-1,10-phenanthroline, 1.13 g (17.78 mmol) of copper powder were added into a three neck round bottom flask with α,α,α-trifluorotoluene and DMSO. When the temperature inside the reaction mixture reached 106° C., 2.4 ml (8.9 mmol) of $C_8F_{17}I$ was added drop wise over 45 min and the reaction was run for 3 hrs. The reaction mixture was allowed to cool to room temperature and 200 ml of chloroform was added. The mixture was then washed with 6×100 ml of concentrated ammonium hydroxide solution, followed by washing with 3×100 ml of D.I. water. The chloroform layer was then collected, dried, and removed to yield crude product, which was further recrystallized from methylene chloride.

Characterization data: $^1$H NMR (CDCl$_3$): δ 9.22 ppm, 8.69 ppm, 7.92 ppm; $^{19}$F NMR (CDCl$_3$); δ −80.62 ppm (t, 6F), −104.61 ppm (m, 4F), −119.79 ppm (m, 4F), −121.09 ppm (m, 4F), −121.58 ppm (m, 4F), −121.76 ppm (m, 4F), −122.58 ppm (m, 4F), −125.98 ppm (m, 4F); MS (LRFAB); m/z (m$^+$) 1016.8 (calcd for $C_{28}H_6F_{34}N_2$: 1016.3).

Example 5

Synthesis of 2,6,9,10-tetrakis-heptadecafluorooctyl-anthracene in HFE-7200

Perfluorooctyl iodide (C$_8$F$_{17}$I, 3.28 ml, 12.4 mmol) was added into a mixture of 2,6,9,10-tetrabromoanthracene (0.494 g, 1 mmol) and copper powder (1.576 g, 24.8 mmol) in HFE-7200® and anhydrous DMSO under nitrogen protection at 90° C. The reaction was monitored by TLC and cooled down to room temperature after 24 hours. The mixture was separated directly to give a HFE-7200® solution of 2,6,9,10-tetrakis-heptadecafluorooctyl-anthracene. Removal of the HFE-7200® solvent yielded the solid product 2,6,9,10-tetrakis-heptadecafluorooctyl-anthracene having characterization data matching that of Example 2.

Example 6

Thin Film Production of 2,6,9,10-tetrakis-heptadecafluorooctyl-anthracene with HFE-7200

5 mg of 2,6,9,10-tetrakis-heptadecafluorooctyl-anthracene was dissolved in 1.0 mL of HFE-7200 and spin coated onto a glass slide a room temperature and atmosphere pressure. The thin film was stable with treatment of water and hydrocarbon based non-halogen solvents, and stable under sunlight (tested with 1.5 AM solar simulator).

Prophetic Example

Synthesis of 2,4,6,8,9,10-hexa-heptadecafluorooctyl-anthracene

Step one: 2,6,9,10-tetrakis-heptadecafluorooctyl-anthracene (1 mmol) is dissolved into 50 ml of HFE-7500® and heated up in a 130° C. oil bath Anhydrous AlBr$_3$ (0.05 mmol) and DBI solid (1.2 mmol) are added into the reaction mixture under string. After 24 hours at 130° C. the reaction mixture will be cooled down to room temperature, and washed with water. The HFE-7500® solution is evaporated to yield 4,8-dibromo-2,6,9,10-tetrakis-heptadecafluorooctyl-anthracene.

Step two: Perfluorooctyl iodide (C$_8$F$_{17}$I, 2.5 mmol) is added into a mixture of 4,8-dibromo-2,6,9,10-tetrakis-heptadecafluorooctyl-anthracene (0.5 mmol) and copper powder (5.0 mmol) in HFE-7500 and anhydrous DMSO under nitrogen protection at 130° C. The reaction is monitored by TLC and cooled down to room temperature after 72 hours. The mixture will be separated directly to give a HFE-7500 solution of 2,4,6,8,9,10-hexa-heptadecafluorooctyl-anthracene. Removal of HFE-7500 will give solid compound 2,4,6,8,9,10-hexa-heptadecafluorooctyl-anthracene.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A fluorinated aromatic compound, wherein the fluorinated aromatic compound is selected from the group consisting of

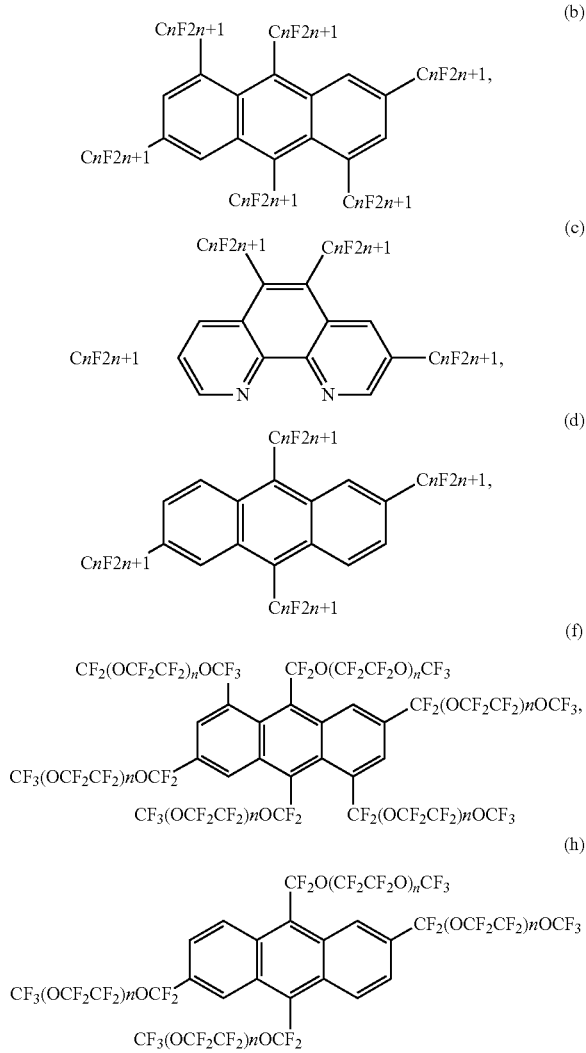

where n is an integer in a range of about 1 to about 30.

2. The fluorinated aromatic compound of claim 1, wherein the fluorinated aromatic compound comprises

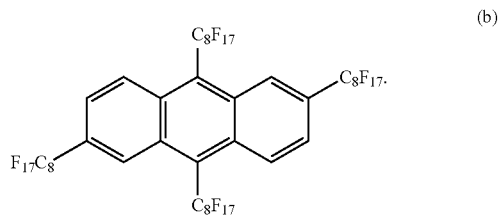

3. A method of making the fluorinated aromatic compound of claim 1, comprising:

combining a halogenated aromatic and a perfluoroalkyl halide in a solvent; and reacting the halogenated aromatic and the perfluoroalkyl halide in a copper mediated cross-coupling reaction.

4. The method of claim 3, wherein the solvent includes one or more of DMF, DMSO, $CH_3CN$, trifluoromethyl benzene or a fluorinated ether.

* * * * *